United States Patent [19]

Mazurek

[11] Patent Number: 4,605,807
[45] Date of Patent: Aug. 12, 1986

[54] PROCESS FOR CATALYTIC CONVERSION OF ETHYLENE TO HIGHER HYDROCARBONS

[75] Inventor: Harry Mazurek, Bala Cynwyd, Pa.

[73] Assignee: Atlantic Richfield Company, Los Angeles, Calif.

[21] Appl. No.: 730,886

[22] Filed: May 6, 1985

Related U.S. Application Data

[63] Continuation-in-part of Ser. No. 605,014, Apr. 27, 1984, abandoned.

[51] Int. Cl.[4] .............................................. C07C 2/02
[52] U.S. Cl. .................................... 585/517; 585/525; 585/528; 585/530; 585/533
[58] Field of Search ............... 585/525, 528, 530, 533, 585/517

[56] References Cited

U.S. PATENT DOCUMENTS

| | | | |
|---|---|---|---|
| 3,827,968 | 8/1974 | Givens et al. | 585/322 |
| 4,150,062 | 4/1979 | Garwood et al. | 585/533 |
| 4,423,268 | 12/1983 | Miller | 585/533 |
| 4,430,516 | 2/1984 | Le Pierre et al. | 585/533 |
| 4,451,685 | 5/1984 | Nevitt et al. | 585/525 |
| 4,456,779 | 6/1984 | Owen et al. | 585/415 |
| 4,499,315 | 2/1985 | Garska et al. | 585/528 |
| 4,511,746 | 4/1985 | Miller | 585/533 |
| 4,511,747 | 4/1985 | Wright et al. | 585/533 |

Primary Examiner—Curtis R. Davis
Attorney, Agent, or Firm—Craig E. Larson

[57] ABSTRACT

A method for converting normally gaseous olefins (esp., ethylene) to normally liquid hydrocarbons wherein the olefin feed is contacted with a siliceous molecular sieve at elevated temperatures and short olefin contact times under high severity conditions favorable for substantial conversion of olefins with maximized liquids productivity. ZSM-5 type zeolites and crystalline borosilicate molecular sieves are particularly preferred catalysts.

19 Claims, 1 Drawing Figure

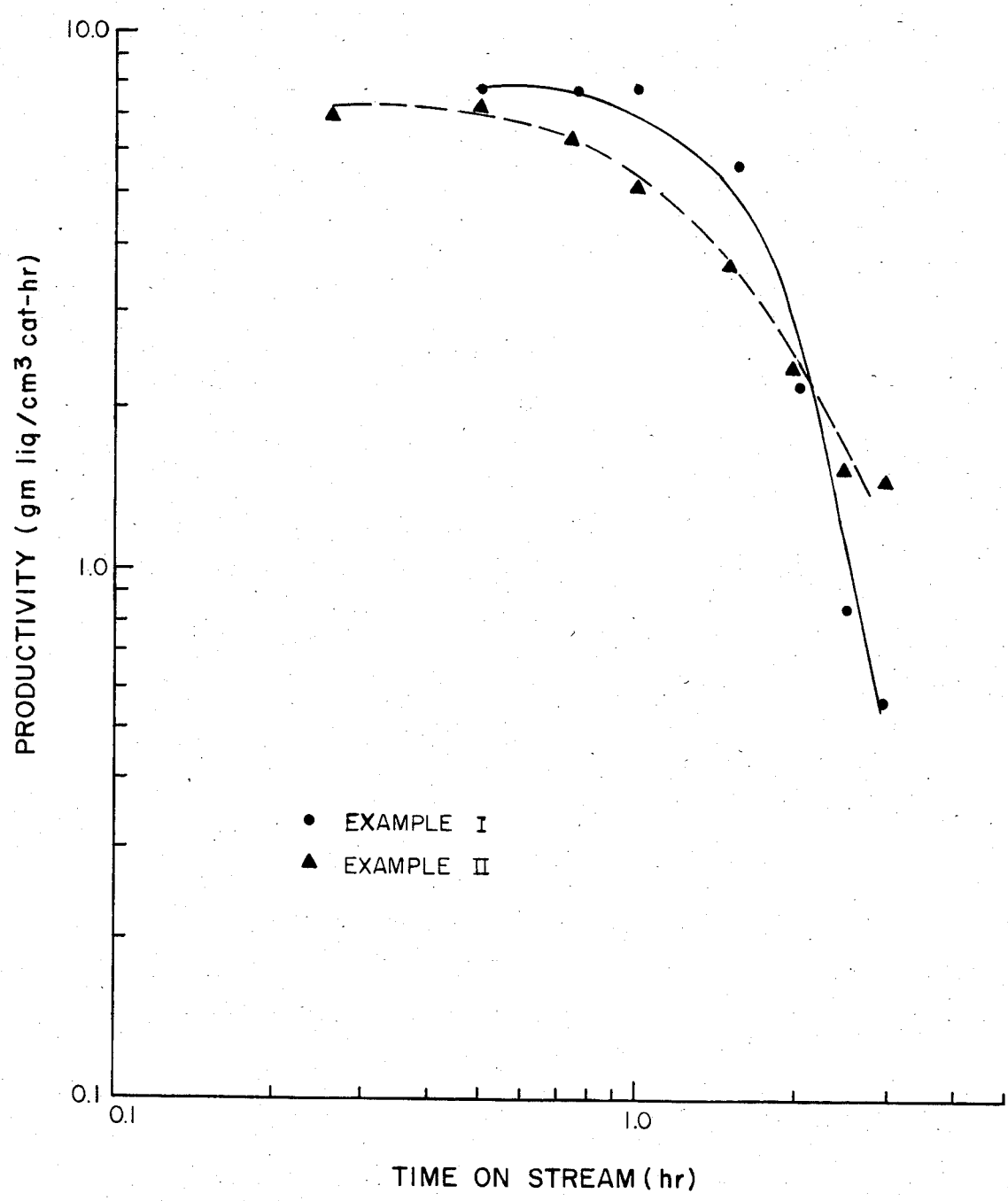

PROCESS FOR CATALYTIC CONVERSION OF ETHYLENE TO HIGHER HYDROCARBONS

CROSS REFERENCE TO RELATED CASE

This application is a continuation-in-part of U.S. patent application Ser. No. 06/605,014, filed Apr. 27, 1984, now abandoned.

BACKGROUND OF THE INVENTION

This invention relates to a method of catalytically converting olefins into higher hydrocarbons. This invention more particularly relates to a method for converting ethylene to higher hydrocarbons by contact with siliceous crystalline molecular sieves. Conversion of various hydrocarbon fractions with acidic catalysts generally and more particularly with siliceous crystalline molecular sieves is well known in the art. The conversions for which such catalysts have been used include cracking, isomerization, hydrocracking, etc. Molecular sieves have also been used for the conversion of hydrocarbon feeds consisting essentially of $C_2$–$C_5$ olefins, mixtures thereof, and mixtures thereof with paraffins to higher molecular weight products.

U.S. Pat. No. 3,325,465 teaches a process for polymerizing olefinic hydrocarbons over zeolites, the initially present cations of which have been partially exchanged with cations selected from the group consisting Co,Ni and rare earth cations. Ethylene polymerization at atmospheric pressure is described in Examples 3–8 of the patent. At column 6, lines 41–47, the patent teaches that use of atmospheric pressure is preferred, although pressures up to 1000 atmospheres may be used. Higher pressures are said to increase throughput but increase the risk of catalyst deactivation. Operating temperatures of 25° to 400° C. and space velocities of 50 to 1000 hr.$^{-1}$ VHSV (volume hourly space velocity), preferably less than 300 hr.$^{-1}$ VHSV, are taught. Hydrocarbon diluents such as paraffins and/or cycloparaffins may be present in the olefinic feedstock, but the patent does not indicate what effect such presence may have on selection of operating parameters for the process.

U.S. Pat. No. 3,760,024 teaches preparation of aromatic compounds by contacting $C_2$–$C_4$ paraffins and/or olefins with a ZSM-5 type zeolite. Operating temperatures of 100°–700° C., operating pressures of 0–1000 psig (preferably 0–500 psig), and space velocities of 0.5–40 hr.$^{-1}$ WHSV (weight hourly space velocity) are taught. The particular combination of operating parameters employed is selected to produce a significant yield of liquid product from a given feedstock, which product is substantially aromatic in nature.

U.S. Pat. No. 3,827,968 discloses an aromatization process wherein the olefin content of a $C_2$–$C_5$ olefin-containing feed is first oligomerized to produce higher molecular weight olefins over a ZSM-5 type zeolite and then contacting the liquid, higher molecular olefins with a zeolite catalyst in a second stage to produce aromatic liquids. The first step of the '968 process differs from the '024 patent in that less severe operating conditions are used to produce a product having a liquid portion consisting principally of $C_5$–$C_9$ olefins. Attempting direct aromatization of certain feedstocks---especially those containing large amounts of paraffins---was apparently found to cause rapid catalyst aging and/or deactivation. Operating conditions employed in the first step of the '968 patent include temperatures of 290°–450° C., pressures up to 800 psig and 0.5–50 hr.$^{-1}$ WHSV. The first stage oligomerization effluent, in addition to olefinic liquids, contains a gas product consisting of a highly paraffinic $C_4$- stream. In addition, the second stage of the '968 process produces an effluent which may contain up to 50% $C_4$- paraffins. The $C_4$-paraffin streams are, according to the '968 patent, preferably recycled to a pyrolysis unit.

U.S. Pat. No. 3,960,978 discloses the conversion of gaseous $C_2$–$C_5$ olefins, either alone or in admixture with paraffins, to a gasoline fraction having no more than about 20 wt. % aromatics by contacting the olefin feed with a ZSM-5 type zeolite having a controlled acid activity (i.e., alpha value) of about 0.1–120. Other oligomerization conditions include temperatures of 260°–480° C. (preferably 290°–450° C.), WHSV of 0.1–25 hr.$^{-1}$ (preferably 0.5–20), and hydrocarbon partial pressures of 0.5 to 40 atmospheres (preferably 0.5–20 atmospheres). An advantage of the process is said to be improved catalyst stability. Example 1 of the patent shows oligomerization of propylene according to the method of the '978 patent. The gaseous product produced was primarily $C_4$ olefins. The patent suggests recycle of the gaseous $C_4$ olefin byproduct to extinction.

U.S. Pat. No. 3,972,832 discloses conversion of aliphatic compounds over phosphorus-containing zeolites. Example 8 of the patent shows that when ethylene is contacted with the phosphorus-containing zeolite at 500° C. and a WHSV of about 1.5, ethylene is converted into propylene and $C_5$ hydrocarbons as the major products. As compared to a zeolite without phosphorus, the olefin/paraffin ratios of the product obtained over the phosphorus-containing zeolite were much higher and the quantity of aromatics produced was much less. Also see U.S. Pat. No. 4,044,065 at column 9, lines 32–48.

U.S. Pat. No. 4,021,502 discloses the conversion of gaseous $C_2$–$C_5$ olefins or mixtures thereof with $C_1$–$C_5$ paraffins to higher molecular weight olefins, over ZSM-4, ZSM-12, ZSM-18, chabazate or zeolite beta. The process is operated under conditions selected to give low yields of aromatics. Temperatures are about 230°–650° C. (preferably 290°–540° C.). WHSV is about 0.2–50 (preferably 1–25). Hydrocarbon partial pressures are about 0.1–50 atmospheres (preferably 0.3–20 atmospheres). An advantage of the process is said to be the stability of the zeolite under the conditions employed.

U.S. Pat. No. 4,070,411 discloses the conversion of lower olefins (e.g., ethylene or propylene) over HZSM-11 catalyst to produce a product having a significant isobutane content. The conversion is effected at temperatures of 300°–500° C. and at space velocities of 0.5–100 WHSV.

U.S. Pat. No. 4,100,218 discloses a process for converting ethane to LPG and gasoline and/or aromatic concentrate by passing olefin effluent from the thermal cracking of ethane over a ZSM-5 type zeolite.

U.S. Pat. No. 4,150,062 discloses the conversion of $C_2$–$C_4$ olefins over ZSM-5 type zeolites in the presence of co-fed water. Temperatures are about 230°–430° C. (preferably 290°–400° C.). Pressures range from atmospheric to 1000 psig (preferably from atmospheric to 450 psig). The WHSV is about 0.2–20 hr.$^{-1}$.

U.S. Pat. No. 4,211,640 teaches conversion of olefinic gasoline fractions over ZSM-5 type zeolites to produce gasoline (having enhanced gum stability) and fuel oil.

U.S. Pat. No. 4,227,992 discloses a process for selectively reacting $C_3$ and higher olefins from a mixture of the same with ethylene to produce products comprising fuel oil and gasoline. Operating conditions are selected such that the $C_3$ and higher olefins are substantially converted to products comprising fuel oil and gasoline but such that substantially no ethylene will be converted. Generally, operating pressures are within the range of about 100–1000 psig, temperatures are within the range of about 150°–315° C., and space velocities are within the range of about 0.1–10 WHSV (based on the $C_3$ and higher olefins).

U.S. Pat. No. 4,451,685 teaches conversion of lower olefins to gasoline blending stocks over borosilicate catalysts.

U.S. Pat. No. 4,423,268 teaches oligomerization of normally gaseous olefins over essentially alumina-free molecular sieves (e.g., silicalite).

As noted, conversion of olefins to gasoline and/or distillate products over a ZSM-5 type catalyst is known. See the description of U.S. Pat. Nos. 3,960,978 and 4,021,502, supra. U.S. Pat. No. 4,227,992 discloses operating conditions for selective conversion of $C_3+$ olefins and no more than 20% ethylene conversion. Closely related is U.S. Pat. No. 4,150,062 which discloses a process of converting olefins to gasoline components. In such processes for oligomerizing olefins using acidic crystalline zeolites, it is known that process conditions may be varied to favor the formation of either gasoline or distillate range products. At moderate temperatures (i.e., 190°– 315° C.) and relatively high pressures (i.e., 42–70 atmospheres) the conversion conditions favor distillate range product having a normal point of at least 165° C. At moderate temperature and relatively lower pressures (i.e., 7–42 atmospheres), the conversion conditions favor gasoline and distillate range products. See U.S. Pat. No. 4,211,640.

One object of the present invention is an improved method for converting ethylene to high yields of heavier hydrocarbons. A more particular object is the production of normally liquid hydrocarbons from ethylene under conditions whereby catalyst productivity is maximized, employing a siliceous crystalline molecular sieve catalyst. Other objects, aspects and the several advantages of the present invention will be apparent to those skilled in the art upon consideration of the following description of this invention and of the appended claims.

SUMMARY OF THE INVENTION

In accordance with the present invention there is provided a process for producing normally liquid hydrocarbons which process comprises contacting a gas comprising ethylene with a siliceous crystalline molecular sieve under high severity conditions including elevated temperatures and short olefin contact times, said conditions being selected such that the liquids productivity of the catalyst is greater than about 50%, preferably greater than about 75%, of the theoretical maximum liquids productivity. In addition to ethylene the feed to the process of this invention may contain other normally gaseous olefins and may also contain other hydrocarbons such as paraffins (e.g. methane and higher alkanes) as well as inorganic components.

Oligomerization of olefins according to the method of this invention has been found to allow substantial olefin conversion to normally liquid hydrocarbons with maximized liquids productivity. One preferred method for carrying the present process comprises continuously recirculating molecular sieve catalyst between an ethylene contact zone and a regeneration zone.

BRIEF DESCRIPTION OF THE DRAWING

The FIGURE is a plot of productivity vs. run time for ethylene contact runs described in Example III.

DETAILED DESCRIPTION OF THE INVENTION

The feedstock converted to normally liquid hydrocarbons according to this invention may contain ethylene and $C_3+$ olefins. In addition, the feedstock may contain other hydrocarbon or non-hydrocarbon components. Examples of other hydrocarbon components include the lower alkanes, especially $C_1$–$C_5$ alkanes. Examples of non-hydrocarbon components include water, carbon oxides (i.e., CO and/or $CO_2$), $N_2$ and the like. The presence of steam in the catalyst reactor zones under the temperature conditions employed is presently believed to substantially effect the aging and/or the deactivation characteristics of the catalyst employed and, accordingly, it is preferred to avoid the the presence of steam in the oligomerization process of this invention. Preferably, the olefins are converted in the substantial absence of hydrogen.

One distinct aspect of the present invention involves the use of highly dilute olefinic feedstocks. More particularly, according to this aspect of the present invention, it has been found that desirable results may be obtained even though the feedstock contains major amounts (i.e., more than 50 vol. %) of lower alkanes. It has further been found that desirable results may be obtained even though the feedstock contains major amounts (i.e., more than 50 vol. %) of methane. When employing such highly dilute olefinic feedstocks in the process of this invention, it has been found advantageous to maintain the ethylene partial pressure in the feed contacted with the catalyst in the oligomerization zone within the range of about 0.5 to 5 atmospheres, preferably within the range of about 1 to 2.5 atmospheres. Total operating pressure in the first reactor zone is thus determined, according to this aspect of the invention, by the ethylene content of the feed to the oligomerization zone. According to this aspect of the present invention such ethylene content may vary broadly, e.g., from less than about 10 vol. % to 50 vol. %.

As will be apparent to those skilled in the art, the selection of whether to employ such highly dilute, olefinic feedstocks or to first isolate an olefinic fraction of such feedstock prior to oligomerization according to this invention, will be dependent on the cost of processing the highly dilute feedstock via oligomerization relative to the cost of isolating an olefinic fraction therefrom. In general, it will noted that alkane recovery from oligomerization effluents (particularly the second catalyst rector zone effluent of the process of this invention) is much easier than isolation before oligomerization.

The process of this invention is particularly suited to oligomerizing feedstocks comprising an olefinic fraction which contains a major amount (i.e., greater than 50 vol. %, preferably greater than 70 vol. %) of ethylene.

One observation that led to the present invention was that operating modes may be selected to maximize the liquids productivity of the molecular sieve oligomerization catalyst. By "liquids productivity" is meant weight of liquid hydrocarbons produced/weight of catalyst/hour or, alternatively, weight of liquid hydrocarbons produced/volume of catalyst/hour. More meaningful comparisons between different molecular sieves are possible using the latter expression of productivity because the densities of the catalysts are widely variable.

A related observation is that operating modes which maximize liquids productivity involve very high severities. Hence, the catalyst deactivates rapidly. However, as will be described in more detail below and as illustrated in the Examples, it is possible to select operating variables to produce the high severities required by the process of this invention which result in sufficiently long periods of operation at high catalyst productivity such that catalyst regeneration may be used to maintain the desired productivities. More specifically, reaction means comprising a system comprising a high-severity oligomerization zone and a catalyst regeneration zone with catalyst preferably continuously recirculating between the two zones is desirably employed to fully exploit the advantages of the broader aspects of this invention.

The broad concept of contacting olefins with a siliceous crystalline molecular sieve to oligomerize the olefins is not novel. A key to one inventive concept of this invention resides in selecting within a limited range of operating conditions such that the following objectives will be accomplished:

(1) ethylene will be substantially converted, i.e., greater than about 50 and preferably greater than about 80 wt % is converted and (2) the products obtained are such that hydrocarbon liquid productivity of the catalyst is maximized.

Maximization of catalyst productivity may be expressed by stating that the liquids productivity of the catalyst is greater than about 50%, preferably greater than about 75% of the theoretical maximum. The theoretical maximum liquids productivity for any given reactor system is obtained by dividing the ethylene feedrate (e.g., grams $C_2=$/hour) by the volume of catalyst present in the reactor.

The characteristics of the normally liquid hydrocarbons produced are not of primary concern in the selection of operating variables. Maintenance of catalyst stability over relatively long run times is not an object of this invention. Rather such catalyst stability is sacrificed in order to maximize liquids productivity.

The general operating parameters for the oligomerization method of this invention can be defined by stating that the conversion is effected at short contact times and that the ethylene feed is introduced to the oligomerization zone at elevated temperatures. By "short contact times" is meant contact times selected within the range of about 0.1-3 seconds, preferably within the range of about 0.1-1 second. By "elevated temperature" is meant a temperature selected within the range of about 285°-425° C., preferably 325°-375° C.

The temperature ranges specified are initial temperatures—the temperatures at which the olefin feed is introduced to the oligomerization zone. Employing the high severities required by the present invention results in highly exothermic reactions. Relatively high exotherms (as much as 300° C. or higher) will occur during oligomerization. Although means (e.g., alkane dilution or staged reactors with interstage cooling) may be employed to reduce the magnitude of such exotherms, such means need not be employed to attain the results of this invention.

Having selected an initial temperature and contact time, operating pressures and space velocities may be selected. Temperature and contact time are considered primary operating variables. Pressure and space velocity are considered secondary operating variables. Generally, however, it has been found desirable to maintain the ethylene partial pressure of the feedstream within the range of about 0.5-5 atmospheres, preferably within the range of about 1-2.5 atmospheres.

These ranges of initial temperature, contact time, pressure and space velocity are not intended to be construed as meaning that all operations within these limits will accomplish the desired results of this invention. What is meant by these units is best expressed in a negative way. Operation outside the ranges set forth will not accomplish the desired results of the process of this invention. A well-known correlation exists between temperature, pressure and space velocity with respect to the severity of the reaction. Stated simply, the present method is concerned with the conversion of ethylene to normally liquid hydrocarbons at a severity such that ethylene is substantially converted and the liquids productivity of the catalyst is maximized. The examples below illustrate such a severity.

To further illustrate, it is known that as contact time is decreased, higher temperatures are necessary to achieve the desired severity. Conversely, as contact time increases, lower temperatures are necessary to achieve the desired severities. Contact time varies directly with pressure and varies inversely with space velocity.

Thus, if the pressure remains constant and space velocity is increased, then a higher temperature is necessary to achieve the desired severity. Conversely, if the space velocity would remain constant and the pressure increased, then a lower temperature is necessary to achieve the desired severity. The precise contact time (and space velocity and pressure) for any given temperature within the broad range previously stated can be easily obtained by routine experimentation following the guidelines and illustrations set forth herein.

One feature of the present invention which is of principal significance to the design of reaction means for carrying out the present process is the relatively rapid deactivation of the catalyst. It has been found that initial catalyst activity may be regenerated and maintained by relatively frequent regeneration of the catalyst during use. Regeneration means per se are conventional and known to those skilled in the art. A preferred reaction system for the present process is one comprising an oligomerization zone and a regeneration zone. Catalyst particles may be provided as fixed, moving, fluidized, ebullating or entrained beds of solids. In the preferred embodiment, solids are provided as fluidized, ebullating or entrained beds of solids with the solids continuously recirculating between the oligomerization and regeneration zones. Average solids residence times in the oligomerization zone preferably is less than 100 minutes, more preferably less than 60 minutes.

Oligomerization effluent produced by the method of this invention generally comprises normally liquid hydrocarbons and will also contain varying amounts of gaseous hydrocarbons. It is within the scope of this invention to recover all or a portion of such gaseous hydrocarbons and recycle them to the oligomerization zone.

Alternatively, it is also within that particular aspect of this invention concerned with oligomerization of olefin feedstocks containing major amounts of ethylene (i.e., a hydrocarbon feed having an olefin fraction containing a major amount of ethylene) to recover and separately convert (e.g. oligomerize) the gaseous hydrocarbon (esp. $C_{3}+$ olefins) present in the oligomerization effluent of the process of this invention.

In a preferred embodiment of this particular aspect of this invention, the hydrocarbons comprising $C_{3}+$ olefins may be converted to normally liquid hydrocarbons in a second oligomerization zone by contact with a siliceous crystalline molecular sieve.

Regarding selection of operating conditions which may be employed in the second oligomerization zone, the general operating parameters for converting $C_{3}+$ olefins to heavier hydrocarbons in the gasoline and/or distillate boiling range can be defined broadly by stating that the conversion is effected at moderate temperature. By "moderate temperature" is meant a temperature selected within the range of about 150°–330° C. The pressure employed in the second oligomerization zone may be vary widely, preferably within the range of about 1 to 70 atmospheres. Similarly, the space velocity may vary widely, preferably within the range of about 0.1 to 50 WHSV. Several alternative objectives are within the scope of operation of the second oligomerization zone: (1) substantial conversion of $C_{3}+$ olefins to normally liquid hydrocarbons; (2) substantial conversion of $C_{3}+$ olefins to olefinic gasoline boiling range hydrocarbons; or (3) substantial conversion of $C_{3}+$ olefins to distillate boiling range hydrocarbons. By "substantial conversion is meant the conversion of at least 80 wt. %, preferably 90 wt. %, of the $C_{3}+$ olefins to said products.

Selection of operating parameters suitable to accomplish any of the foregoing objectives have previously been described in the particular context of oligomerization using ZSM-5 type zeolites. See, for example, U.S. Pat. No. 3,760,024 (describes conversion of $C_2$–$C_4$ paraffins and/or olefins); U.S. Pat. No. 3,960,978 (describes conversion of $C_2$–$C_5$ of olefins to a gasoline fraction containing no more than about 20 wt. % aromatics); U.S. Pat. No. 4,021,502 (describes conversion of gaseous olefins to higher molecular weight olefins over ZSM-4, ZSM-12, ZSM-18 chabazite or zeolite beta); and U.S. Pat. No. 4,227,992 (describes selective oligomerization of $C_{3}+$ olefins to produce fuel oil and gasoline products). The entire content of each of these applications is incorporated by reference.

The comments made above concerning the effect of varying operating temperature, pressure, and space velocity on severity of the first oligomerization zone apply generally to the effect of such operating conditions on severity in the second oligomerization zone.

Furthermore, the foregoing descriptions of how to use ZSM-5 type zeolites in the process of this invention have been found to also apply to the similar use of other siliceous crystalline molecular sieves. Moreover, the use of borosilicate, silicoaluminophosphate, and silicalite catalysts in the present process constitute distinct aspects of the broader invention generally described herein.

The catalyst employed in the method of this invention are siliceous crystalline molecular sieves. Such silica-containing crystalline materials include materials which contain, in addition to silica, significant amounts of alumina. These crystalline materials are frequently named "zeolites", i.e., crystalline aluminosilicates. However, the use of materials exemplified by silicoaluminophosphates (see U.S. Pat. No. 4,440,871) are also within the scope of this invention. Silica-containing crystalline materials also include essentially aluminum-free silicates. These crystalline materials are exemplified by crystalline silica polymorphs (e.g., silica silicalite, disclosed in U.S. Pat. No. 4,061,724 and organosilicates disclosed in U.S. Pat. No. RE. 29948), chromiasilicates (e.g., CZM), ferrosilicates and galliosilicates (see U.S. Pat. No. 4,238,318), and borosilicates (see U.S. Pat. Nos. 4,226,420; 4,269,813; and 4,327,236).

The term "essentially aluminum-free" is not intended to totally exclude the presence of aluminum from the catalyst composition. For example, it has been suggested that silicates containing less than 100 ppm. by weight of aluminum may not be effective for the oligomerization of olefins. See U.S. Pat. No. 4,331,641, especially see column 9, lines 49–52 of that patent.

Crystalline aluminosilicate zeolites are best exemplified by ZSM-5 (see U.S. Pat. Nos. 3,702,886 and 3,770,614), ZSM-11 (see U.S. Pat. No. 3,709,979) ZSM-12 (see U.S. Pat. No. 3,832,449), ZSM-21 and ZSM-38 (see U.S. Pat. No. 3,948,758), ZSM-23 (see U.S. Pat. No. 4,076,842), and ZSM-35 (see. U.S. Pat. No. 4,016,246).

The acidic crystalline aluminosilicates are desirably in the hydrogen form, although they may also be stabilized or their performance otherwise enhanced by ion exchange with rare earth or other metal cations.

The molecular sieves can be composited with inorganic matrix materials, or they can be used with an organic binder. It is preferred to use an inorganic matrix since the molecular sieves, because of their large internal pore volumes, tend to be fragile, and to be subject to physical collapse and attrition in normal loading and unloading of the reaction zones as well as during oligomerization processes.

Preferred siliceous crystalline molecular sieves to be employed in the process of this invention are ZSM-5 type zeolites, borosilicates and silicalite. ZSM-5 and borosilicates are particularly preferred.

The present invention is further illustrated by reference to the following examples.

EXAMPLE I

A crystalline borosilicate catalyst was prepared by dissolving $H_3BO_3$ and NaOH in distilled $H_2O$. Then tetra-n-propylammonium bromide (TPAB) was added and dissolved. Finally, Ludox AS-30(30% solids) was added with vigorous stirring. The addition of Ludox gave a curdy, gelatinous, milky solution. This solution was placed in a vessel and sealed. The vessel was heated to 329° F. (165° C.) for 7 days. At the end of this time, it was opened and its contents were filtered. The recovered crystalline material was washed with copious quantities of $H_2O$ and was then dried at 329° F. (165° C.) in a forced air oven.

The material was calcined at 1,100° F. (593° C.) in air for 4 hours to remove the organic base. The calcined sieve was exchanged one time with an aqueous solution of $NH_4NO_3$ and then a second time with an aqueous ammonium acetate solution at 190° C. (88° C.) for 2 hours. The exchanged borosilicate was dried and calcined in air by heating it to 900° F. (482° C.) in 4 hours, maintaining the borosilicate at 900° C. (482° C.) for 4 hours and then cooling to 100° F. (38° C.) in 4 hours.

The X-ray diffraction pattern is presented in Table I below.

TABLE I

| Interplanar Spacing (Å) | Relative Intensity Spacing |
|---|---|
| 3.34 | 9 |

TABLE I-continued

| Interplanar Spacing (Å) | Relative Intensity Spacing |
|---|---|
| 3.30 | 10 |
| 3.24 | 5 |
| 3.04 | 14 |
| 2.97 | 15 |
| 2.93 | 7 |
| 2.72 | 5 |
| 2.60 | 7 |
| 2.48 | 8 |
| 2.00 | 15 |
| 1.99 | 17 |
| 1.91 | 6 |
| 1.86 | 5 |
| 1.66 | 5 |

EXAMPLE II

An aluminosilicate catalyst was prepared by dissolving 400 grams of N-Brand sodium silicate in 300 ml. of water. Then 150 grams of NaCl, 14.2 grams of $Al_2(SO_2)_3 \cdot H_2O$, and 32.9 grams of $H_2SO_4$ was dissolved in 680 ml of $H_2O$. Tetrapropyl ammonium bromide (50 grams) was dissolved in 200 ml of $H_2O$. The sodium silicate solution was mixed with the sodium chloride solution to form a thick, semi-solid mass which was mixed well. The bromide solution was then added to the mixture. The mixture (250 ml.) was charged to an autoclave and was maintained with stirring at 300° F. for 16 hours.

The mixture had a pH of about 12. The solids were washed and decanted until no positive Cl-test was shown with $AgNO_3$. The solids were calcined at 500° C. to product a white solid.

The material was identified by X-ray diffraction as having the typical ZSM-5 pattern. The X-ray diffraction pattern is presented in Table 2.

TABLE 2

| Interplanar Spacing (Å) | Relative Intensity |
|---|---|
| 11.47 | 21 |
| 10.16 | 18 |
| 6.80 | 3 |
| 6.41 | 6 |
| 6.02 | 12 |
| 5.64 | 10 |
| 5.03 | 6 |
| 4.64 | 5 |
| 4.29 | 9 |
| 3.86 | 100 |
| 3.74 | 59 |
| 3.67 | 38 |
| 3.45 | 12 |
| 3.35 | 12 |
| 3.07 | 18 |
| 3.00 | 18 |
| 2.75 | 6 |
| 2.61 | 9 |
| 2.50 | 9 |
| 2.41 | 9 |
| 2.01 | 20 |
| 1.88 | 5 |
| 1.67 | 7 |

EXAMPLE III

The physical characteristics of the materials of Examples I and II were tested and are presented in Table 3 below.

TABLE 3

| | Bulk Density | Al content, wt % | Acidity meq. $NH_3$/gm |
|---|---|---|---|
| Example I | 0.622 | 0.14 | 0.4 |
| Example II | 0.214 | 1.5 | 0.5 |

EXAMPLE IV

Ethylene-contact runs were made at atmospheric pressure at temperatures between 300°–369° C. in a stainless steel tube reactor packed with 5 ml. of catalyst. The reactors were brought up to temperature under a flow of heated nitrogen which is switched to ethylene at the start of the run. The ethylene-contact runs described had a duration as indicated.

Samples were taken during the run after 10 min, 15 min, 30 min, and one hour. The samples were analyzed and the results are presented in Table 4 below. The effluent was collected and measured and analyzed from which a cumulative sample was generated. At the end of each ethylene-contact run, the reactor was flushed with nitrogen to cool the reactor and catalyst.

The FIGURE is a plot of instantaneous results obtained during ethylene contact runs 2 and 3 described in Table 2.

TABLE 4

| | Run 1 | Run 2 | Run 3 |
|---|---|---|---|
| Catalyst | Example II | Example II | Example I |
| Run Time (hr) | 1 | 3 | 3 |
| Temp (°C.) | 350–528 | 350–549 | 353–507 |
| Contact Time (sec) | 0.45 | 0.52 | 0.53 |
| WHSV ($hr^{-1}$) | 39.2 | 39.2 | 12.7 |
| Pressure, psig | 60 | 60 | 60 |
| $C_2=$ Conv (%) | 95.1 | 60.8 | 57.5 |
| Wt. % Selectivity | | | |
| $CH_4$ | 1.3 | 0.5 | 0.1 |
| $C_2$ | 4.0 | 0.01 | <0.01 |
| $C_3=$ | 4.2 | 10.7 | 10.8 |
| $C_3$ | 10.9 | 7.8 | 4.2 |
| $C_4=$ | 5.3 | 10.7 | 11.0 |
| $C_4$ | 2.9 | 60 | 5.9 |
| $C_5+$ | 68.1 | 64.2 | 68.0 |
| Coke | 0.2 | 0.1 | 0.02 |
| Productivity | | | |
| (# liq./# Cat-hr) | 27.8 | 15.5 | 4.9 |
| (gm liq./$cm^3$ cat-hr) | 5.9 | 3.3 | 3.2 |

What is claimed is:

1. A process for converting ethylene to normally liquid hydrocarbons which comprises contacting a gas comprising ethylene with a siliceous crystalline molecular sieve under high severity conditions including elevated temperatures and short olefin contact times, said conditions being selected such that the liquids productivity of the catalyst is greater than about 50% of the theoretical maximum.

2. The process of claim 1 wherein the temperature is selected within the range of about 285° to 425° C.

3. The process of claim 1 wherein the contact time is selected within the range of about 0.1 to 3 seconds.

4. The method of claim 3 wherein the ethylene partial pressure in the feed is within the range of about 0.5 to 5 atmospheres.

5. The method of claim 1 wherein the molecular sieve is an acid ZSM-5 type catalyst.

6. The method of claim 5 wherein said conditions are selected such that the liquids productivity of the catalyst is greater than about 75% of the theoretical maximum.

7. The method of claim 1 wherein the molecular sieve is an essentially aluminum-free siliceous crystalline molecular sieve.

8. The method of claim 1 wherein the molecular sieve is a borosilicate.

9. The method of claim 8 wherein said conditions are selected such that the liquids productivity of the catalyst is greater than about 75% of the theoretical maximum.

10. The method of claim 1 wherein the molecular sieve is a silicate.

11. The method of claim 1 wherein the molecular sieve is a silicoaluminophosphate.

12. The method of claim 1 wherein normally gaseous, $C_3+$ hydrocarbons are recovered from the effluent produced by said contacting and are contacted in a second oligomerization zone with a siliceous crystalline molecular sieve at moderate temperature under conditions favorable for conversion of $C_3+$ olefins to a second oligomerization effluent stream rich in heavier hydrocarbons in the gasoline or distillate boiling range.

13. The method of claim 1 wherein said molecular sieve is at least periodically regenerated.

14. The method of claim 13 wherein said molecular sieve continuously recirculates between an olefin contact zone and a regeneration zone.

15. The process of claim 1 wherein the gas contacted with the molecular sieve comprises an olefinic fraction containing greater than 50 volume percent ethylene.

16. The process of claim 1 wherein the gas contacted with the molecular sieve comprises an olefinic fraction containing greater than 70 volume percent ethylene.

17. The process of claim 1 wherein the temperature is selected within the range of about 325°–375° C.

18. The process of claim 1 wherein the contact time is selected within the range of about 0.1 to 1 second.

19. The process of claim 8 wherein ethylene is converted in the substantial absence of hydrogen.

* * * * *